(12) United States Patent
Worley

(10) Patent No.: US 10,597,350 B2
(45) Date of Patent: Mar. 24, 2020

(54) PROCESS FOR RECOVERING BYPRODUCTS FROM MMA

(71) Applicant: Dow Global Technologies LLC, Midland, MI (US)

(72) Inventor: William G. Worley, Missouri City, TX (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 16/096,730

(22) PCT Filed: May 15, 2017

(86) PCT No.: PCT/US2017/032587
§ 371 (c)(1),
(2) Date: Oct. 26, 2018

(87) PCT Pub. No.: WO2017/205089
PCT Pub. Date: Nov. 30, 2017

(65) Prior Publication Data
US 2019/0127312 A1    May 2, 2019

Related U.S. Application Data

(60) Provisional application No. 62/341,245, filed on May 25, 2016.

(51) Int. Cl.
*C07C 67/54* (2006.01)

(52) U.S. Cl.
CPC .................................. *C07C 67/54* (2013.01)

(58) Field of Classification Search
USPC ......................................................... 560/218
See application file for complete search history.

(56) References Cited

FOREIGN PATENT DOCUMENTS

JP         03532763          5/2004

OTHER PUBLICATIONS

Machine translation JPH11302224, 2004.*

* cited by examiner

*Primary Examiner* — Ana Z Muresan
(74) *Attorney, Agent, or Firm* — Brian L. Mutschler

(57) ABSTRACT

The present invention provides methods comprising distilling a reaction mixture of methacrolein and methanol used to make methyl methacrylate (MMA) in the presence of one or more strong or inorganic acids, the mixture comprising an aqueous organic component mixture of all of water, MMA, methacrolein methanol and acetals or hemiacetals of methacrolein to remove the acetals or hemiacetals of methacrolein to a level of 100 ppm or below, based on the amount of methyl methacrylate. The method reduces the amount of acetals or hemiacetals of methacrolein to well below equilibrium levels and eliminates the need for additional downstream distillation to refine the product of the reaction.

9 Claims, 1 Drawing Sheet

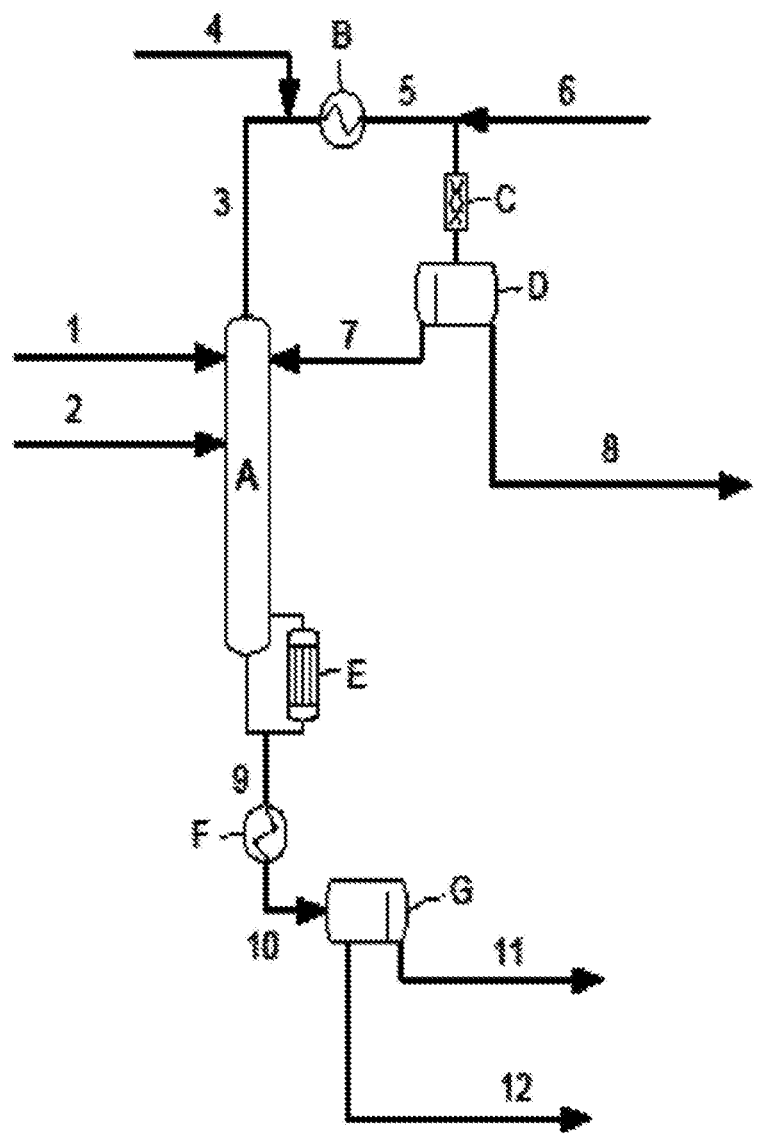

PROCESS FOR RECOVERING BYPRODUCTS FROM MMA

The present invention relates to methods comprising distilling a feed stream of an aqueous organic component mixture containing methyl methacrylate (MMA), water, methanol, methacrolein and at least 1 wt. %, such as at least 3 wt. %, of acetals or hemiacetals of methacrolein, based on the total weight of MMA plus the acetals or hemiacetals of methacrolein in the aqueous organic component mixture, for example, in a distillation column, reacting the aqueous organic component mixture with one or more strong or inorganic acids having a pKa of 1 or less or, preferably, 0 or less, and removing from the distillation an overhead stream and a bottoms stream comprising methyl methacrylate and 100 ppm or less, preferably, 25 ppm or less, or, more preferably, less than 5 ppm of acetals or hemiacetals of methacrolein.

Various synthetic routes are known in the formation of methyl methacrylate (MMA). No matter the route used, it is desirable to maximize MMA yield by recovering byproducts of the reaction, such as acetals and hemiacetals in the reaction of methacrolein and methanol to form MMA. Because the acetals boil at around 106° C., it remains very difficult to remove such a by-product from MMA by distillation, thereby adversely affecting MMA product purity.

Japan patent no. JP03532763B2, to Asahi discloses processes to remove methacrolein dimethyl acetal (MDA) from a feed taken from an oxidative esterification reactor effluent in the making of MMA. In the first step, one removes the bulk of the excess methanol and unreacted methacrolein overhead in a distillation column, a methanol recovery column) and the MMA from the column bottoms (crude MMA), which can contain some aqueous phase. The bottoms stream, which has two-phases, is treated with an inorganic acid to catalyze MDA hydrolysis to methanol and methacrolein, thereby reducing the MDA content of the MMA to <20 ppm. However, getting to such a low MDA level relies on having a relatively low MDA content, e.g. 0.49 wt. % MDA on a MMA basis in the feed, per the Asahi example 1. Because the hydrolysis of the acetal is an equilibrium reaction, as the MDA content of the crude MMA increases, so does the MDA content post hydrolysis. Following the Asahi method taught in Example 1 of the patent, if a feed contains 12 wt. % MDA, based on the total weight of MMA plus MDA, the resulting post hydrolysis mixture has 150 ppm MDA (results at 70° C., equilibrium is affected by temperature). This would be an unacceptable impurity level in MMA.

Accordingly, the need remains for improved removal of byproducts of the reaction of methacrolein and methanol to form MMA.

The present inventors have endeavored to improve the removal of acetals or hemiacetals of methacrolein from the reaction of methacrolein and methanol to make methyl methacrylate.

SUMMARY OF THE INVENTION

1. In accordance with the present invention, methods for removing by products in a reaction to make methyl methacrylate comprise (a) distilling a feed stream of an aqueous organic component mixture containing methyl methacrylate, water, methanol, methacrolein and at least 1 wt. %, or up to 20 wt. %, or, preferably, 2 wt. % or more, for example, 3 wt. % or more, or, preferably, up to 15 wt. %, of acetals or hemiacetals of methacrolein, based on the total weight of MMA plus the acetals or hemiacetals of methacrolein in the aqueous organic component mixture, for example, in a distillation column comprising a lower section, a middle section and an upper section by feeding the aqueous organic component mixture to the upper section of the distillation column; (b) reacting the aqueous organic component mixture with one or more strong or inorganic acids having a pKa of 1 or less or, preferably, 0 or less, such as by feeding the strong or inorganic acid into the distillation column, or, preferably, the middle section or the upper section of the distillation column, such as a point at or above the midpoint that marks halfway between the bottom and the top of distillation column, or, preferably, the upper section of the distillation column, and (c) removing from the distillation each of an overhead stream and a bottoms stream comprising methyl methacrylate and 100 ppm or less, preferably, 25 ppm or less, or, more preferably, less than 5 ppm of acetals or hemiacetals of methacrolein, for example, by removing each such stream separately from the distillation column.

2. The method of the present invention as set forth in item 1, above, further comprising reboiling the bottoms stream in a reboiler and recirculating the reboiled bottoms stream into the distillation or distillation column.

3. The method of the present invention as set forth in item 2, above, wherein a residence time in the reboiler of the aqueous organic component mixture and the strong or inorganic acid ranges from 1 minute to 120 minutes or, preferably, from 2 to 50 minutes.

4. The method of the present invention as set forth in any one of items 1, 2, or 3, above, wherein the strong or inorganic acid is chosen from sulfuric acid, sulfonic acids, halogen containing inorganic acids, nitric acids, and other protic acids having a pKa of 1 or less or, preferably, 0 or less.

5. The method of the present invention as set forth in any one of items 1, 2, 3, or 4, above, wherein the amount of the one or more strong or inorganic acid ranges from 0.01 to 5.0 wt. % or, preferably, from 0.05 to 0.5 wt. %, based on the total weight of water in the feed stream of the aqueous organic component mixture and in the one or more strong or inorganic acids.

6. The method of the present invention as set forth in any one of items 1, 2, 3, 4, or 5, further comprising combining the overhead stream with a polymerization inhibitor, such as phenothiazine, in a solvent, such as methanol.

7. The method of the present invention as set forth in any one of items 1, 2, 3, 4, 5 or 6, above, further comprising, cooling the overhead stream, such as by condensing it using a coolant, such as water, running the cooled overhead stream through a mixer, such as a static mixer, and decanting the overhead stream to remove the aqueous phase, followed by recirculating the organic phase of the overhead stream comprising methacrolein back to the upper section of the distillation column.

8. The method of the present invention as set forth in any one of items 1, 2, 3, 4, 5, 6, or 7, above, further comprising cooling the bottoms stream, such as by condensing it using a coolant, such as water, and decanting the thus cooled bottoms stream to separate the resulting crude methyl methacrylate (crude MMA) stream from the resulting waste water stream.

9. In the method of the present invention as set forth in any one of items 1, 2, 3, 4, 5, 6, 7, or 8, above, wherein the distillation column comprises trays or packing.

10. In the method of the present invention as in item 9, above, wherein the distillation column comprises from 10 to 50 trays or, preferably, from 20 to 40 trays, or an equivalent number of equilibrium stages in a packed column.

BRIEF DESCRIPTION OF THE DRAWING

The FIGURE is a schematic of a method of the present invention.

All percentage compositions are weight percentages (wt. %), and all temperatures are in ° C., unless otherwise indicated.

Unless otherwise indicated, all temperatures are room temperature (21-23° C. and all pressures are standard pressure (~101 kPa or ~760 mm/Hg).

As used herein, "at least one" and "one or more" are used interchangeably. The terms "comprises," "includes," and variations thereof do not have a limiting meaning where these terms appear in the description and claims.

The singular forms "a," "an," and "the" include plural referents unless the context clearly dictates otherwise.

All phrases comprising parentheses denote either or both of the included parenthetical matter and its absence. For example, the phrase "(meth)acrylate" includes, in the alternative, acrylate and methacrylate.

As used herein, the term "gas chromatography" or "GC" refers to methods used to analyze materials and amounts of such materials using methods in which the samples are diluted 10:1 in acetone and are characterized using an Agilent 6890N GC instrument calibrated per the manufacturers recommendations (Agilent Technologies, Santa Clara, Calif.) and equipped with a flame ionization detector and a Restek Stabilwax™ (a distribution of polyethylene glycol having a formula weight of from 400 to 20,000 g/mol, Restek Corporation, Bellefonte, Pa.) column (30 m×0.32 mm ID×1 μm $d_f$), wherein "ID" means inner diameter and "$d_f$" means film thickness. In the GC method, a 1 μL volume of each sample was injected via capillary split injection at a ratio of 20:1 into an injector port set at 225° C.; initial column temperature was 50° C., with an equilibrium time of 1 minute and an initial hold time of 6 minutes, followed by heating at a rate of 10° C./min to achieve a 215° C. final temperature, with a final hold time of 2 minutes to give a total run time of 24.5 minutes; column and initial flow rates were 1.8 ml/min Helium constant flow.

As used herein, the term "ppm" means part per million by weight.

The present invention allows for essentially complete reversal of the formation of acetals or hemiacetals of methacrolein during reaction of methacrolein and methanol and allows for the simultaneous recovery of methanol and methacrolein for reuse to make more methyl methacrylate (MMA). The invention comprises reacting the mixture in the distillation column with one or more strong or inorganic acids in a hydrolysis reaction. In the present invention, the strong acid is added to a distillation column to which is fed the effluent of a reaction, such as from an oxidative esterification reactor, from which excess methanol and unreacted methacrolein are being removed. Performing the methods of the present invention inside the distillation column allows one to "break" the equilibrium limitations of the hydrolysis reaction. Thus, in accordance with the present invention, the inventors have discovered methods to break the equilibrium constraints of the hydrolysis reaction of methacrolein dimethylacetal to produce methacrolein and methanol. Therefore, the by products of reaction are removed in a distillation column, at the same time as the reaction is occurring. For example, a 12 wt. % proportion of methacrolein dimethyl acetal or hemiacetal (MDA) on a crude MMA basis can be reacted down to less than 20 ppm. In contrast, if the methods are performed outside the distillation, the equilibrium limit would be no level below 140 ppm of MDA. Another advantage of the invention is that it combines a distillation column suitable remove methanol and methacrolein produced by a hydrolysis reaction of an acetal or hemiacetal of methacrolein with the strong or inorganic acid with an apparatus useful in performing the hydrolysis reaction.

In the reaction of methanol and methacrolein to form methyl methacrylate, the main constituent of the contents at the bottom of the distillation column is methyl methacrylate, whereas the concentration of the methanol and methacrolein contained by the vapor is higher at the vicinity of the top of the column.

Any suitable strong or inorganic acid is useful in the present invention as long as the acid is strong enough to effect reaction in reasonable time. Such acids include sulfuric acid, sulfonic acids, such as organosulfonic acids like p-toluene sulfonic acid or alkylsulfonic acids, e.g. methanesulfonic acid, halogen containing inorganic acids like hydrochloric acid, nitric acids, and other protic acids having a pKa of 1 or less or, preferably, 0 or less.

As shown in the FIGURE, an aqueous organic component mixture or feed stream (1) which contains methyl methacrylate, water, methanol, methacrolein and acetals or hemiacetals of methacrolein, such as methacrolein dimethyl acetal (MDA), is fed to the top section of distillation column (A). Separately, an aqueous mixture (2) comprising a strong or inorganic acid is fed into distillation column (A), which may be, for example, at or above the midpoint that marks halfway between the bottom and the top of distillation column (A). In distilling the aqueous organic component mixture (1), a bottoms stream (9) is formed which is methyl methacrylate and acetals or hemiacetals of methacrolein; and an overhead stream (3) is formed as a second aqueous organic component mixture comprising water, methanol and methacrolein. Overhead stream (3), which has an optional inlet (4) for a polymerization inhibitor is then run through a condenser (B) using cooling water to bring the overhead stream (3) down to the temperature of the cooling water; then, the cooled overhead stream (5) is combined with a water feed (6) and is run through a static mixer (C) and is decanted in decanter (D) to remove the aqueous phase, including methanol, which is removed at outlet (8). The organic phase (7) from decanter (D), which contains methyl methacrylate, methacrolein, and hexane, is recirculated back into the top of distillation column (A). Reboiler (E) heats the contents of the column and fuels the distillation. The product bottoms stream (9) is run through cooler (F) and is cooled thereby, resulting in a cooled bottoms stream (10) that is decanted in bottoms decanter (G) to separate the resulting waste water stream (12) from the crude methyl methacrylate (crude MMA) stream (11) which contains less than 100 ppm of acetals or hemiacetals of methacrolein.

The distillation column includes an inlet for feeding an aqueous mixture comprising a strong or inorganic acid into the distillation column to react with the aqueous organic component mixture that contains methyl methacrylate, water, methanol, methacrolein and acetals or hemiacetals of methacrolein.

Preferably, at least a part of the aqueous organic component mixture is heated at the bottom of the distillation column by a reboiler to form vapor that ascends in the distillation column, exchanging heat and reacting with the aqueous organic component mixture flowing down in the distillation column. Therefore, Suitable distillation columns used to separate water, methacrolein and methanol from the aqueous organic component mixture can be selected according to criteria well known to those skilled in the art. For example, a distillation column can include trays or packing, such as low pressure drop wire gauze structured packing.

In accordance with the present invention, the use of hexane is not required. Distillation methods without the use of an entrainer solvent will work equally well to react out the acetals/hemiacetals in the feed.

The distillation column may have anywhere from 10 to 50 trays or, preferably, from 20 to 40 trays. More trays will work, but are not needed. Packing can be used in the place of trays as is conventional in the art.

In the methods of the present invention, the temperature and pressure in the distillation column is dependent on the composition of the material being distilled. For example, the distillation column is operated at a pressure, such as from 50 to 500 kPa, or from 65 to 110 kPa. The unit, 1 atmosphere is equivalent to 101 kPa. The reboiler temperature advantageously is from 60 to 110° C., or, preferably, from 80 to 90° C.

EXAMPLES

The following chemical abbreviations were used: MMA=methyl methacrylate; MAn=methacrolein; MDA=methacrolein dimethylacetal; HEX=Hexane; MeOH=methyl alcohol; 4-hydroxy tempo=4-hydroxy-2,2,6,6-tetramethylpiperidin-1-oxyl; MSA=Methanesulfonic Acid.

Example 1: Distillation to Remove Methyl Methacrylate from the Reaction of Methacrolein and Methanol Lab experiments were carried out to demonstrate the present invention. The distillation column was run at atmospheric pressure (101 kPa or 760 mmHg). The reboiler pressure depends on the pressure drop across the column, which ran about 15 to 20 mmHg across a 30 tray column, so the reboiler pressure was about 775 to 780 mmHg, resulting in a process side temperature of 84° C. at the bottom of the column.

To insure that the distillation apparatus was able to process the aqueous organic feed stream without flooding or using an excessively long reboiler/sump residence time, the feed stream comprised a lower methanol content than in a large scale apparatus, while still maintaining the proper concentration in the lower portions of the distillation column.

In Example 1, strong acid was added so that the acid content fed to the column based on the total amount of fluid fed into the column was 980 ppm (of the aqueous organic feed stream and the strong or inorganic acid feed stream) and resulted in a pH of 2.8 (12, FIGURE). Aqueous strong acid was added to the distillation column at tray 24, counting from bottom to top, of 30 trays. In the feed stream, the total amount of MDA/(MMA+MDA) was 12.1 wt. %. The residence time in the reboiler was 30 minutes. The makeup of various streams in the distillation apparatus are shown in Table 1, below. The product of the treated methyl methacrylate bottoms stream was 16 ppm MDA, as measured by gas chromatography (GC).

TABLE 1

Stream Contents in the Methods of the Present Invention

| Component | Reference No. (FIGURE) (all proportions are wt. %) | | | | | | | |
|---|---|---|---|---|---|---|---|---|
| | 1 | 2 | 4 | 6 | 7 | 8 | 11 | 12 |
| Water | 14.50 | 99.50 | | 99.96 | 0.0 | 60.27 | 1.2 | balance |
| Methanol | 30.48 | | 99% | | 2.1 | 34.54 | | 0.05 |
| Methyl Methacrylate | 47.61 | | | | 28.6 | 2.82 | 98.8 | 1.43 |
| Methacrolein dimethylacetal | 6.56 | | | | 2.82 | 0.01 | 16 ppm | |
| Methacrolein | 0.24 | | | | 6.9 | 2.06 | | |
| Methyl Formate | 0.42 | | | | 0.36 | 0.29 | | |
| Hexane | | | | | 59.20 | 0.004 | | |
| Methanesulfonic Acid | | 0.50 | | | | | | |
| 4-Hydroxy Tempo | 0.04 | | 1 | 0.04 | | | | |
| Flow (g/hr) | 195.8 | 6.9 | 3.3 | 96.5 | 190.0 | 185.6 | 84.1 | 21.6 |

Example 2

Example 1 was repeated except with a lower content of MDA to start with. In Example 2, the acid content fed to the column based on the total fluid feed was 1040 ppm. Aqueous strong acid was added to the distillation column at tray 24, counting from bottom to top, of 30 trays. In the feed stream, the total amount of MDA/(MMA+MDA) was 5.4 wt. %. The residence time in the reboiler was 30 minutes. The makeup of various streams in the distillation apparatus are shown in Table 2, below. The product of the treated methyl methacrylate bottoms stream (Reference 11) was <3 ppm, as measured by GC.

TABLE 2

Stream Contents in Low MDA Methods of the Present Invention

| Component | Reference No. (FIGURE) (all proportions are wt. %) | | | | | | | |
|---|---|---|---|---|---|---|---|---|
| | 1 | 2 | 4 | 6 | 7 | 8 | 11 | 12 |
| Water | 14.50 | 99.50 | | 99.96 | | | | |
| Methanol | 34.13 | | 99 | | | | | |
| Methyl Methacrylate | 48.11 | | | | | | | |
| Methacrolein | 2.75 | | | | | | | <3 |

TABLE 2-continued

Stream Contents in Low MDA Methods of the Present Invention

| Component | Reference No. (FIGURE) (all proportions are wt. %) | | | | | | | |
|---|---|---|---|---|---|---|---|---|
| | 1 | 2 | 4 | 6 | 7 | 8 | 11 | 12 |
| dimethylacetal | | | | | | | | ppm |
| Methacrolein | 0.09 | | | | | | | |
| Methyl Formate | 0.15 | | | | | | | |
| Hexane | | | | | | | | |
| Methane-sulfonic Acid | | 0.50 | | | | | | |
| Phenothiazine | | | | 1 | | | | |
| 4-Hydroxy Tempo | 0.04 | | | | 0.04 | | | |
| Flow (g/hr) | 196.0 | 7.4 | 6.0 | 96.2 | 180.0 | 192.9 | | |

Comparative Example 1

A process using a reactor downstream of a distillation column used to remove methanol and methacrolein from an aqueous organic mixture containing methyl methacrylate (similar to Example 1 of Japan patent no. JP03532763B2) was performed to show the utility of the present invention. The reaction was carried out in a 50 ml roundbottom flask agitated with a polytetrafluoethylene (Teflon™ polymer, Chemours, Wilmington, Del.) coated spin bar operated at 70° C. for a period of 30 minutes to treat an aqueous methyl methacrylate stream containing around 10.8 wt. %, based on the weight of methyl methacrylate, of methacrolein dimethyl acetal (MDA). A sample of 14.8 g of the 10.8% MDA in MMA was contacted with 4.8 g of 5 wt. % sulfuric acid solution in the reactor. After 30 minutes, the MDA content was reduced to 150 ppm, as measured by GC, based on MMA plus MDA.

I claim:

1. A method comprising distilling a feed stream of an aqueous organic component mixture containing methyl methacrylate (MMA), water, methanol, methacrolein and at least 1 wt. % of acetals or hemiacetals of methacrolein, based on the total weight of MMA plus the acetals or hemiacetals of methacrolein in the aqueous organic component mixture, reacting the aqueous organic component mixture with one or more strong or inorganic acids having a pKa of 1 or less and removing from the distillation an overhead stream and a bottoms stream comprising methyl methacrylate and 100 ppm or less of acetals or hemiacetals of methacrolein.

2. The method as claimed in claim 1, wherein the one or more strong or inorganic acids is chosen from sulfuric acid, sulfonic acids, halogen containing inorganic acids, nitric acids, and other protic acids having a pKa of 1 or less.

3. The method as claimed in claim 1, wherein the one or more strong or inorganic acids has a pKa of 0 or less.

4. The method as claimed in claim 1, wherein the reacting comprises (a) distilling a feed stream of an aqueous organic component mixture containing methyl methacrylate, water, methanol, methacrolein and at least 1 wt. % of acetals or hemiacetals of methacrolein, based on the total weight of MMA and acetals or hemiacetals of methacrolein in the aqueous organic component mixture, in a distillation column comprising a lower section, a middle section and an upper section by feeding the aqueous organic component mixture to the upper section of the distillation column; (b) feeding the strong or inorganic acid into the middle section or the upper section of the distillation column to react the aqueous organic component mixture with the one or more strong or inorganic acids, and (c) removing from the distillation each of an overhead stream and a bottoms stream comprising methyl methacrylate and 100 ppm or less of acetals or hemiacetals of methacrolein.

5. The method as claimed in claim 1, comprising reboiling the bottoms stream and recirculating the reboiled bottoms stream into the distillation.

6. The method as claimed in claim 1, wherein a residence time of the aqueous organic component mixture and the strong or inorganic acid together in the distillation and in any reboiler ranges from 5 seconds to 90 minutes.

7. The method as claimed in claim 1, wherein the amount of the one or more strong or inorganic acid ranges from 0.1 to 5.0 wt. %, based on the total weight of acetals or hemiacetals of methacrolein in the feed stream of an aqueous organic component mixture.

8. The method as claimed in claim 3, wherein the distillation column comprises trays or packing.

9. The method as claimed in claim 6, wherein the distillation column comprises from 10 to 50 trays or an equivalent number of equilibrium stages in a packed column.

* * * * *